(12) United States Patent
Huang et al.

(10) Patent No.: US 8,959,985 B2
(45) Date of Patent: Feb. 24, 2015

(54) MICROPARTICLE DETECTING APPARATUS

(75) Inventors: Chun-ming Huang, Hsinchu (TW);
Chen-chia Chen, Hsinchu (TW);
Chi-sheng Lin, Hsinchu (TW);
Chien-ming Wu, Hsinchu (TW)

(73) Assignee: National Applied Research Laboratories, Hsinchu (TW)

( * ) Notice: Subject to any disclaimer, the term of this patent is extended or adjusted under 35 U.S.C. 154(b) by 273 days.

(21) Appl. No.: 13/547,061

(22) Filed: Jul. 12, 2012

(65) Prior Publication Data

US 2013/0291628 A1  Nov. 7, 2013

(30) Foreign Application Priority Data

May 7, 2012  (TW) .............................. 101116249 A

(51) Int. Cl.
*G01N 15/10* (2006.01)
(52) U.S. Cl.
USPC ........................................ 73/61.71; 73/61.73
(58) Field of Classification Search
CPC .......... G01N 15/0272; G01N 15/0656; G01N 15/1245; B01D 25/08
See application file for complete search history.

(56) References Cited

U.S. PATENT DOCUMENTS

| | | | | |
|---|---|---|---|---|
| 2,910,406 | A | * | 10/1959 | Novak ........................... 424/529 |
| 4,542,518 | A | | 9/1985 | Anthony |
| 4,755,287 | A | * | 7/1988 | Jones ............................ 209/355 |
| 7,846,743 | B2 | | 12/2010 | Tai et al. |
| 2009/0101559 | A1 | | 4/2009 | Bala Subramaniam et al. |
| 2009/0188864 | A1 | | 7/2009 | Zheng et al. |
| 2010/0315628 | A1 | * | 12/2010 | Mertsching et al. .......... 356/301 |

FOREIGN PATENT DOCUMENTS

| | | |
|---|---|---|
| TW | 385010 U | 3/2000 |
| TW | 200538735 A | 12/2005 |
| TW | 200638039 A | 11/2006 |
| TW | 201116308 A | 5/2011 |
| TW | 201119726 A | 6/2011 |

OTHER PUBLICATIONS

X. Yang, J. M. Yang, Y. C. Tai, C. M. Ho, "Micromachined membrane particle filters", Sensors and Actuators 73 (1999) 184-191.
B. Lu, S. Zheng, B. Q. Quach, Y. C. Tai, "A Study of the Autofluorescence of Parylene Materials for µTAS Applications", Lab on a Chip, 10 (2010) 1826-1834.

* cited by examiner

*Primary Examiner* — Paul West
(74) *Attorney, Agent, or Firm* — Mark M. Friedman

(57) ABSTRACT

A microparticle detecting apparatus is disclosed and includes at least one detection unit, each of which includes: a first sieve having at least a first mesh, a separator stacked on one side of the first sieve and having a separator hole, and a second sieve stacked on one side of the separator and having several second meshes. The diameter of the second mesh is smaller than that of the first mesh, and the first and second meshes are misaligned with each other in a vertical direction of the first and second sieves. The detection unit further includes at least a sensor aligned with the first or second mesh for detecting microparticles trapping into the first mesh or passing through the second mesh. Therefore, the microparticle detecting apparatus is suitably used for detecting or counting any microparticles with different size, to effectively shorten the detection processes of sample fluids.

7 Claims, 9 Drawing Sheets

MICROPARTICLE DETECTING APPARATUS

FIELD OF THE INVENTION

The present invention relates to a microparticle detecting apparatus, and more particularly to a microparticle detecting apparatus having sensors to detect or count microparticles.

BACKGROUND OF THE INVENTION

Accordingly, the methods of counting cell numbers include hemocytometer, flow cytometer, protein quantitative analysis and enzyme-linked immunosorbent assay (ELISA), etc., but all of these methods of counting cell numbers, as described above, exist some defects. For example, a hemocytometer is used to count cell numbers by manpower, so that errors due to mis-operation of operators are frequent. If there is a small amount of cells, the accuracy of counting cell numbers by hemocytometer may be affected. Further, when counting cell numbers by a flow cytometer, not only cells must be pre-treated to react to immunofluorescent staining antibody, but also an immunofluorescent antibody detecting system taking much cost must be used. Furthermore, the column of the flow cytometer can pass only single cell each time, so that it is not easy to increase the counting rate of cells, while the particle size of cells cannot be identified by the flow cytometer. Others, the main defect of these two techniques of protein quantitative analysis and ELISA, which are applied to cell counting, is that it needs to convert into cell concentration calculated by regression curve equation, and thus the detecting error is remained. As described above, it is necessary to improve the conventional methods of cell counting.

Recently, with the development of Micro Electro-Mechanical System (MEMS), various miniature biochemical devices are researched and developed in the world. For example, Taiwan Invention Publication No. 201119726, entitled "Filter Structure and Method for Filtrating" is disclosed, wherein the filter structure comprises a first porous film having a plurality of first holes; and a second porous film having a plurality of second holes and disposed on the first porous film, wherein the diameter of the second holes is smaller than that of the first holes. The filter structure can drain water by an easy and power-saving method, such as compressing. Further, the foregoing invention also provides a method for filtration comprising steps of: providing the above-mentioned filter structure; and guiding a mixed solution to flow downward onto a top surface of the second porous film of the filter structure, wherein residues having a size greater than that of the second holes in the mixed solution are intercepted, and a liquid in the mixed solution passes through the second holes and keeps flowing down. The major feature of the above-mentioned invention is to provide a filter structure for separating the solids and liquids, and to provide excellent venting efficiency and avoid the problem of blocking holes due to filtrated residues. However, the filter structure of the above-mentioned invention has no sensor element, and thus it cannot further count the microparticles after filtration.

Furthermore, Taiwan Invention Pat. No. 1257480, entitled "Cellular Micro-particle Detection Chip and Manufacturing Method Thereof" is disclosed, wherein the cellular microparticle detection chip is suitable for counting and classifying cells in a sample fluid. The cellular microparticle detection chip comprises a transparent plate-like base, a hollow micro-channel unit formed in the base, and a sensing unit installed in the micro-channel unit. The micro-channel unit comprises a sample channel having a front end communicated with a through hole formed on the surface of the base for the mentioned sample fluid to flow therein; two limiting flow channels separately arranged at both sides of the sample channel and having distal ends communicated with a distal end of the sample channel for water fluid to flow therethrough; a fusion channel having a front end communicated with distal ends of the sample channel and the limiting flow channels for fusing and guiding the sample fluid and water fluid; at least one laser channel installed at one side of the fusion channel and communicated with an exterior of the base; and at least one photo-sensitive channel installed at the other side of the detecting channel, having an inner end axially corresponding to the laser channel and communicated with the exterior of the base. Therefore, the major feature of the above-mentioned invention pattern is to provide a laser optic fiber and a photo-sensitive optic fiber to be sensor units of the micro-channel unit. When cells in the sample fluid pass through a space between the laser optic fiber and the photo-sensitive optic fiber, the light signals are changed and transmitted to the exterior of the base through the photo-sensitive optic fiber after detection, so as to carry out the cell detection. However, in fact, the structure of the cellular micro-particle detection chip according to the above-mentioned invention patent is more complicated, and the manufacture process thereof involves in various precise techniques. Thus, if wanting to achieve the standard yield of bio-medical detection chips, it must waste more manufacturing cost.

According to the above-mentioned methods existed disadvantages, including fail to counting accurately, get complicated structure or unable to reduce manufacturing cost, etc. As a result, it is necessary to provide a microparticle detecting apparatus to solve the problems existing in the conventional technologies.

SUMMARY OF THE INVENTION

A primary object of the present invention is to provide a microparticle detecting apparatus, which is provided with sensors corresponding to meshes for detecting the microparticles that falls into the meshes in a sample fluid, in order to simultaneously detect the numbers of the target microparticles in real-time when the target microparticles are passively separated, so that the detecting processes can be simplified and shortened.

A secondary object of the present invention is to provide a microparticle detecting apparatus, wherein there are three methods which can be chosen to install the sensors in the microparticle detecting apparatus, and the whole structure is simplifier and easier to manufacture, so that it is advantageous to expand the application fields and increase the product functions.

To achieve the above object, the present invention provides a microparticle detecting apparatus which comprises at least one detection unit, and each of which comprises:

a first sieve having at least one first mesh;

a separator stacked on one side of the first sieve and having a separator hole;

a second sieve stacked on one side of the separator and having a plurality of second meshes, wherein the diameter of the second meshes is smaller than that of the first mesh, and the first mesh and the second meshes are misaligned with each other in a vertical direction of the first and second sieves; and at least one sensor aligned with the first mesh or the second meshes, and detecting microparticles falling into the first mesh or passing through the second meshes.

In one embodiment of the present invention, materials of the first and second sieves are simultaneously selected from Si, SiC or glass.

In one embodiment of the present invention, material of the separator is selected from Si, SiC, glass, photoresist, polyimide or cyclic olefin copolymer; wherein material of the separator 12 can be selected from the same materials of the first and second sieves 11, 13, but not limited thereto.

In one embodiment of the present invention, the sensor comprises a plurality of first sensors, the first sensor is mounted on one side of the first sieve opposite to the second meshes, and the diameter of the first sensor is greater than that of the second meshes.

In one embodiment of the present invention, the at least one sensor comprises at least one second sensor, the second sensor is mounted on one side of the second sieve opposite to the first mesh, and the diameter of the second sensor is greater than that of the first mesh.

In one embodiment of the present invention, the microparticle detecting apparatus is further cooperated with a container, a recording device, an automatic injecting/pumping device and a light emitting unit, wherein a sample fluid passes through the first mesh, the separator hole and the second meshes in turn, while the at least one sensor detects and then transmits variation values of photocurrent caused by the microparticles to the recording device for recording.

In one embodiment of the present invention, the sensor is selected from a silicon (Si) photodiode sensor, the sensor detects the variation values of photocurrent caused by the microparticles and shading light emitted from the light emitting unit.

Furthermore, the present invention further provides a microparticle detecting apparatus which is further cooperated with a container, a recording device, an automatic injecting/pumping device and two magnetic field modules, wherein a sample fluid passes through the first meshes, the separator hole and the second meshes in turn, wherein the at least one sensor detects and then transmits variation values of giant magnetoresistance caused by the microparticles to the recording device for recording.

In another embodiment of the present invention, the microparticle detecting apparatus further comprises a magnetic micro-beads kit which labels one type of the microparticles in the sample fluid to be one type of magnetic microparticles.

In another embodiment of the present invention, the sensor is selected from a giant magnetoresistance (GMR) sensor, and the sensor detects and transmits the variation values of giant magnetoresistance (GMR) to the recording device for recording, wherein the variation values of giant magnetoresistance are caused by the microparticles passing through a magnetic field generated from the magnetic field modules.

The above-mentioned arrangement of the sensors according to the present invention, the microparticle detecting device can detect or count microparticles of different sizes in the same sample fluid in a real-time manner, so as to expand the application field of the product, increase the product function and satisfy various market requirement. And, in comparison with the conventional techniques using fluorescent detecting system, the operation cost of the present invention is more economical and has higher market competitiveness.

DETAILED DESCRIPTION OF THE PREFERRED EMBODIMENTS

The structure and the technical means adopted by the present invention to achieve the above and other objects can be best understood by referring to the following detailed description of the preferred embodiments and the accompanying drawings. Furthermore, directional terms described by the present invention, such as upper, lower, front, back, left, right, inner, outer, side, longitudinal/vertical, transverse/horizontal, and etc., are only directions by referring to the accompanying drawings, and thus the used directional terms are used to describe and understand the present invention, but the present invention is not limited thereto.

Figures 1, 2A:
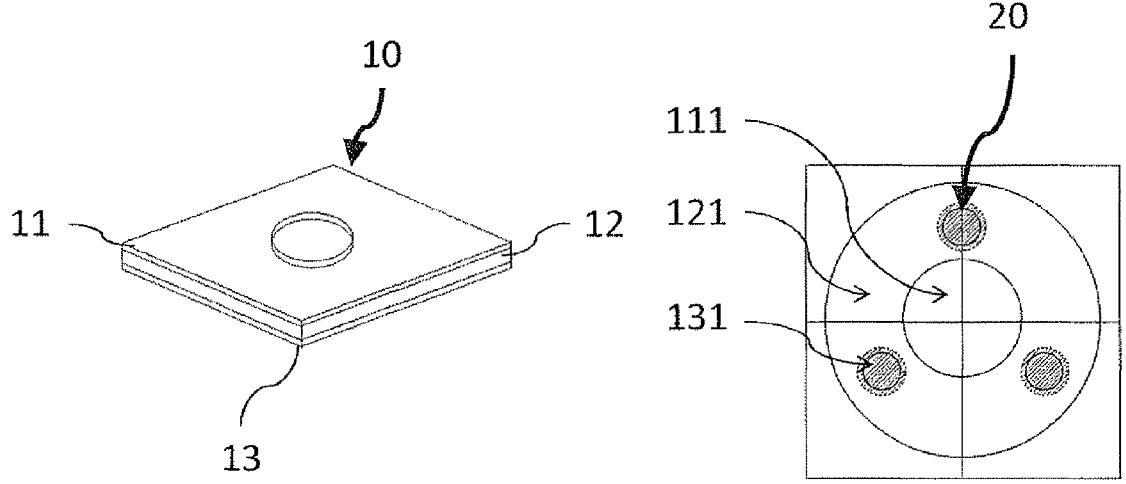
FIG. 1 is an assembled perspective view of a detection unit of a microparticle detecting apparatus of the present invention.
FIG. 2A is a top view of a microparticle detecting apparatus according to a first embodiment of the present invention.
Figure 2B:
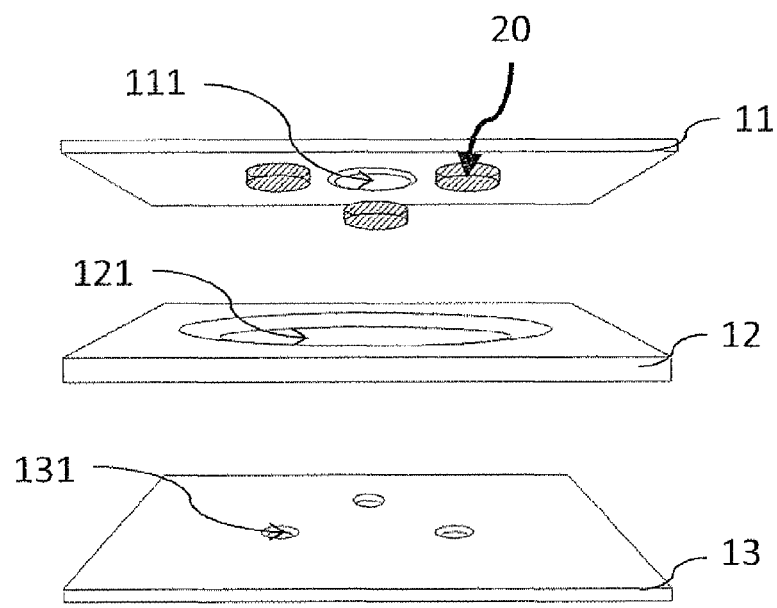
FIG. 2B is an exploded perspective view of the microparticle detecting apparatus according to the first embodiment of the present invention.

Referring now to FIGS. 1, 2A and 2B, a microparticle detecting apparatus according to a first embodiment of the present invention is illustrated and comprises at least one detection unit 10, and each of which comprises a first sieve 11, a separator 12, a second sieve 13 and at least one first sensor 20. The first sieve 11 has at least one first mesh 111. The separator 12 is stacked on one side of the first sieve and has a separator hole 121. The second sieve 13 is stacked on one side of the separator and has a plurality of second meshes 131, wherein the diameter of the second meshes 131 is smaller than that of the first mesh 111, and the first mesh 111 and the second meshes 131 are misaligned with each other in a vertical direction of the first and second sieves. The first sensor 20 is opposite to and aligned with the second meshes, and detects microparticles which pass through the second meshes 131.

Referring still to FIGS. 2A and 2B, the microparticle detecting apparatus according to a first embodiment of the present invention is illustrated, wherein materials of the first and second sieves 11, 13 are simultaneously selected from Si, SiC or glass; material of the separator 12 is selected from Si, SiC, glass, photoresist (such as SU-8), polyimide or cyclic olefin copolymer. And, the material of the separator 12 can be preferably selected from the same materials of the first and second sieves 11, 13, but not limited thereto. Furthermore, the embodiment comprises a plurality of the first sensor 20, the first sensors 20 are mounted on one side of the first sieve 11 opposite to the second meshes 131. Therefore, the microparticle detecting apparatus according to the first embodiment is suitable to detect or count the microparticles passing through the second meshes 131.

Figure 3A:
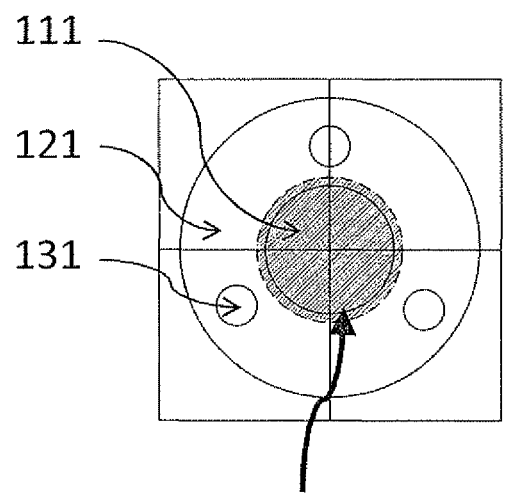
FIG. 3A is a top view of a microparticle detecting apparatus according to a second embodiment of the present invention.
Figure 3B:
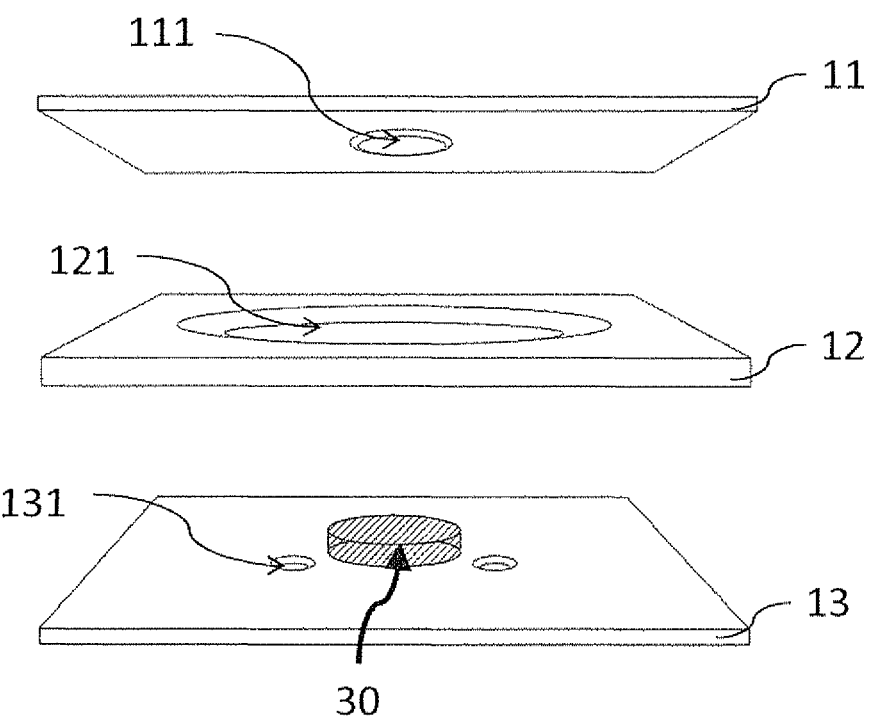
FIG. 3B is an exploded perspective view of the microparticle detecting apparatus according to the second embodiment of the present invention.

Referring to FIGS. 3A and 3B, the microparticle detecting apparatus according to a second embodiment of the present invention is illustrated, wherein the basic structure and selected materials of the first sieve 11, the second sieve 13 and the separator 12 are substantially similar to the first embodiment. However the second embodiment comprises at least one a second sensor 30, wherein the second sensor 30 is mounted on one side of the second sieve 13 opposite to one side of the first mesh 111, and the diameter of the second sensor 30 is greater than that of the first mesh 111. Therefore, the microparticle detecting apparatus according to a second embodiment of the present invention is suitable for detecting or counting the microparticles falling into the first mesh 111.

Figure 4A:
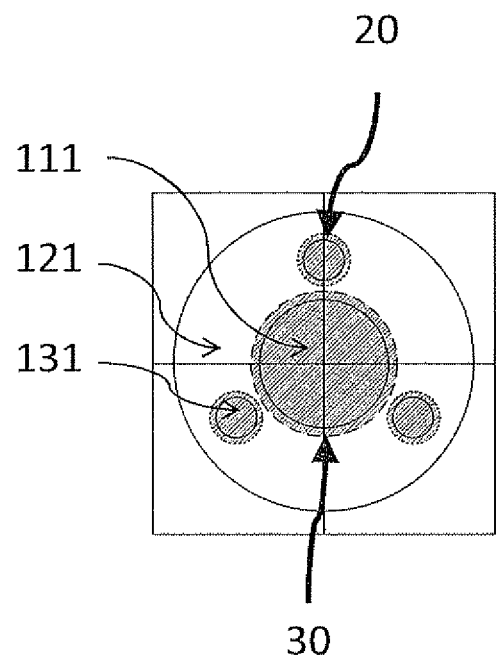
FIG. 4A is a top view of a microparticle detecting apparatus according to a third embodiment of the present invention.
Figure 4B:
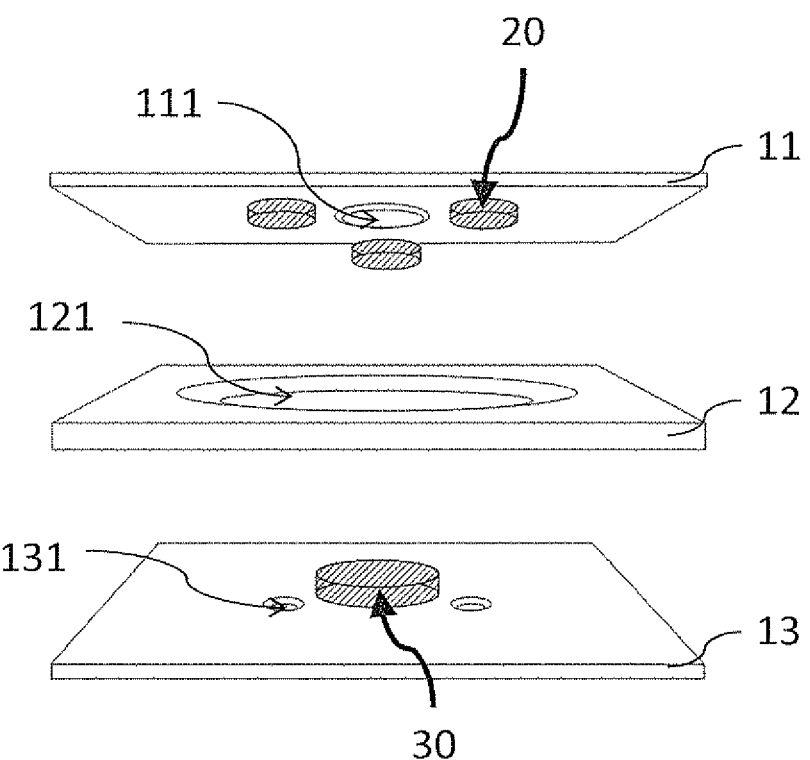
FIG. 4B is an exploded perspective view of the microparticle detecting apparatus according to the third embodiment of the present invention.

Moreover, referring to FIGS. 4A and 4B, the microparticle detecting apparatus according to a third embodiment of the present invention is illustrated, wherein the basic structure and selected materials of the first sieve 11, the second sieve 13 and the separator 12 are substantially similar to the first embodiment, but the third embodiment simultaneously comprises a plurality of first sensors 20 and at least one a second sensor 30. Therefore, the microparticle detecting apparatus according to the third embodiment of the present invention is suitable for simultaneously detecting or counting the microparticles falling into the first mesh 111, and/or the microparticles passing through the second meshes 131. Thus, it further provides the double-check function of counting. Further, in the microparticle detecting apparatus of the present invention, one sensor is mounted on and opposite to each of the meshes, so that the microparticle detecting apparatus can count a cell one by one.

Figure 5:
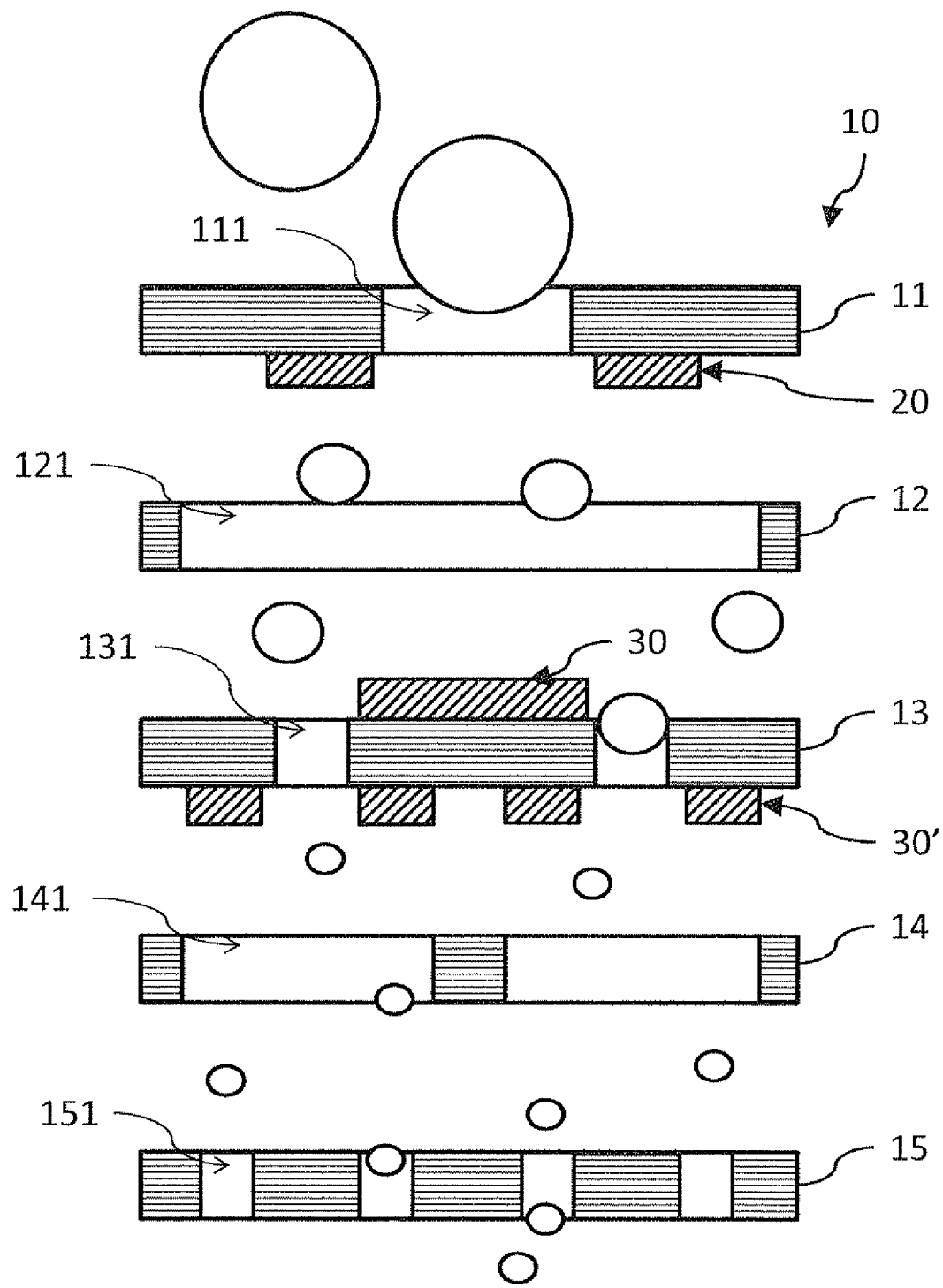
FIG. 5 is an exploded cross-sectional view of a microparticle detecting apparatus according to a forth embodiment of the present invention.

Referring to FIG. 5, the microparticle detecting apparatus according to a forth embodiment of the present invention is illustrated, wherein the basic structure and selected materials of the forth embodiment are substantially similar to the first embodiment, but the microparticle detecting apparatus of the forth embodiment comprises a plurality of the same structures of the detecting units 10, such as including the detecting unit 10 arranged on a 2×2 array, but the number is not limited thereto, for example, it also can be 2, 3, 5, 9 or more. Furthermore, the detecting unit 10 can extend and increase numbers of the sieves and the separator according to actual requirement. For example, each of the detecting units 10 comprises a first sieve 11, a first separator 12, a second sieve 13, a second separator 14 and a third sieve 15, and is simultaneously provided with a plurality of first sensor 20, a plurality of second sensor 30 and a plurality of third sensor 30', wherein the first sieve 11, the first separator 12, the second sieve 13, the second separator 14, the third sieve 15 forms first meshes 111, first separator holes 121, second meshes 131, second separator holes 141 and third meshes 151, respectively. The first sensor 20 is mounted to one side of the first sieve 11 opposite to the second mesh 131; the second sensor 30 is mounted to one side of the second sieve 13 opposite to the first mesh 111; and the third sensor 30' is mounted on the other side of the second sieve 13 opposite to the third mesh 151.

In the present embodiment, according to the microparticle detecting apparatus provided by the present invention, the size of the meshes is defined according to the size of the specific microparticles which are selected, so that the design of each sieve layers in the microparticle detecting apparatus of the present invention is provided with different sensors facing meshes of different diameters, so as to provide a function of simultaneously sieving microparticles of different sizes. In other words, the second sensor 30 can detect microparticles with the largest diameter corresponding to the diameter of the first mesh 111; the first sensor 20 can detect microparticles with secondary greater diameter corresponding to the diameter of the second mesh 131; and the third sensor 30' can detect microparticles with the smallest diameter corresponding to the diameter of the third mesh 151.

Figure 6:
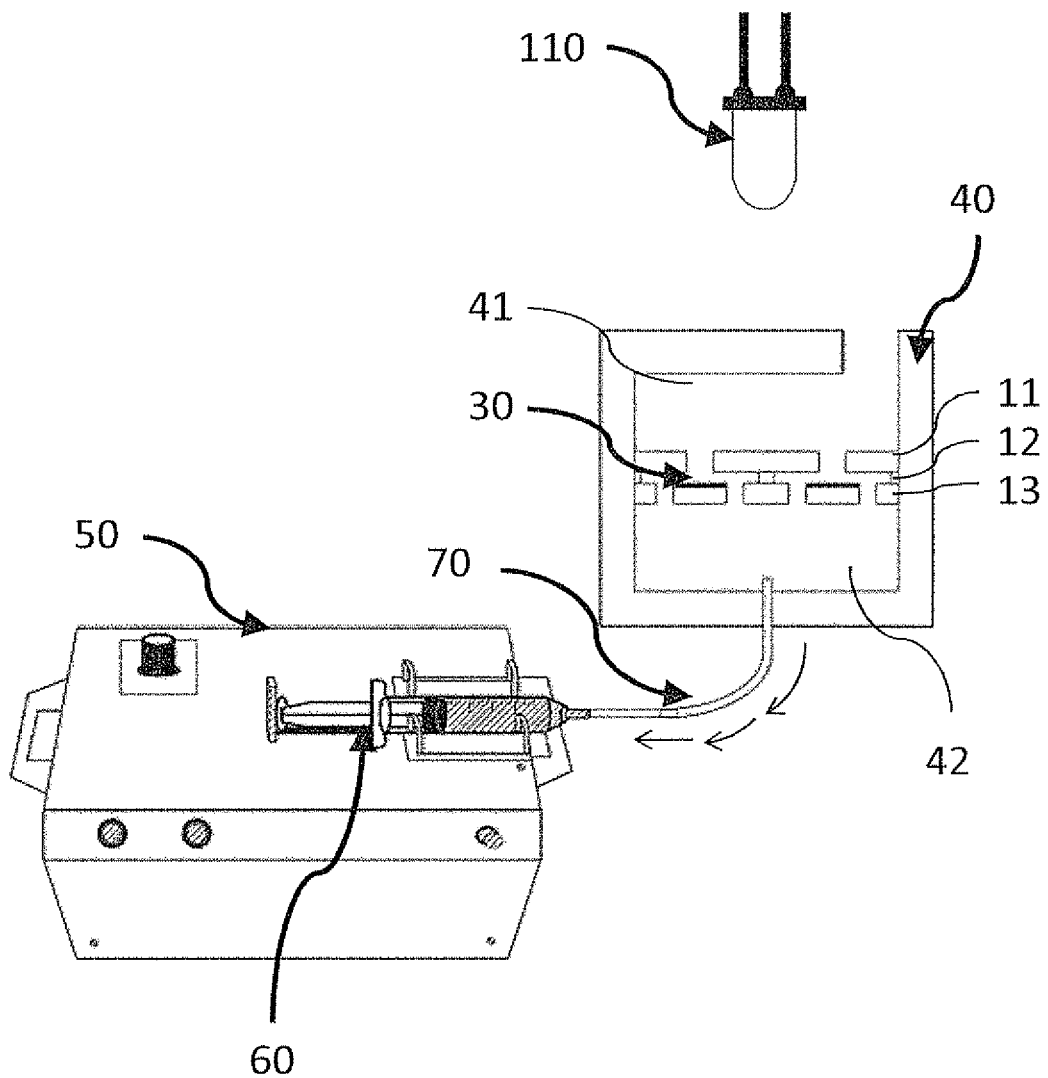
FIG. 6 is a schematic view of a microparticle detecting apparatus according to a fifth embodiment of the present invention.

Referring to FIG. 6, the microparticle detecting apparatus according to a fifth embodiment of the present invention is substantially similar to FIGS. 3A and 3B of the second embodiment, wherein the microparticle detecting apparatus of the fifth embodiment comprises at least one second sensor 30, and is further cooperated with a container 40, an automatic injecting/pumping device 50, a recording device 60, and a light emitting unit 110, wherein the container 40 is a tank made of plate material of transparent resins, such as polydimethylsiloxane (PDMS). The microparticle detecting apparatus is fixed into the container 40 and used to separate an inner space of the container 40 into a first tank 41 and a second tank 42.

Furthermore, in the embodiment, the automatic injecting/pumping device 50 is communicated with the second tank 42 of the container 40 through a pipe 70. The automatic injecting/pumping device 50 can be set to automatically inject or pump. The second sensor 30 is selected from a silicon photodiode sensor, and the second sensor 30 is electrically connects to the recording device 60. The light emitting unit 110 is used to emit a light, and the light can pass through the first mesh 111 to be detected values of photocurrent by the second sensor 30, and then transmitted to the recording device 60 by the second sensor 30.

Figure 7A:
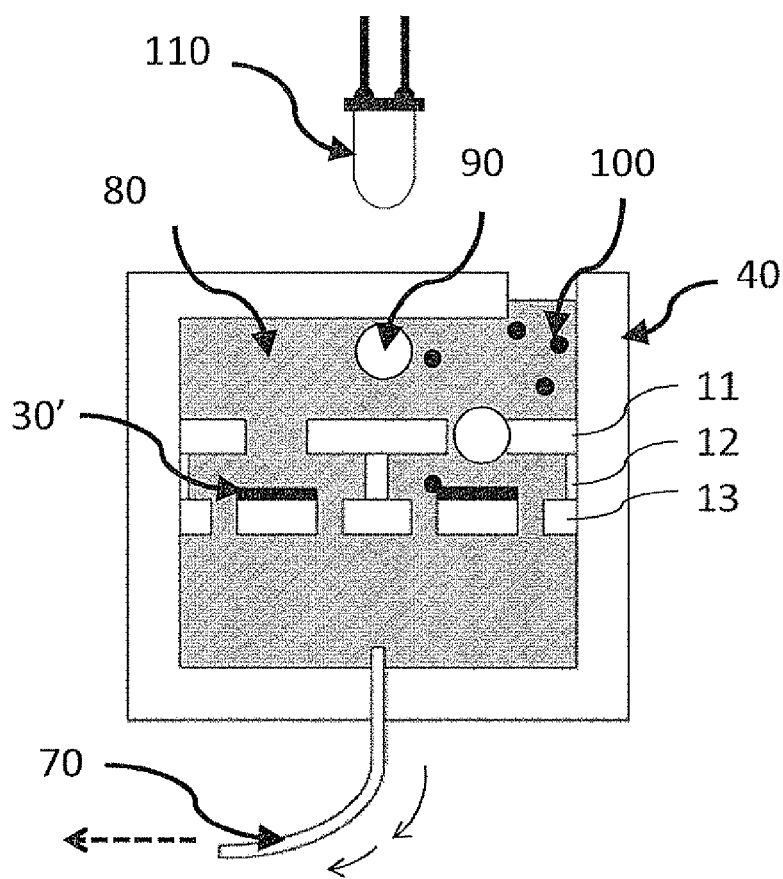
FIG. 7A is an operational view of the microparticle detecting apparatus before reaction according to the fifth embodiment of the present invention.
Figure 8A:
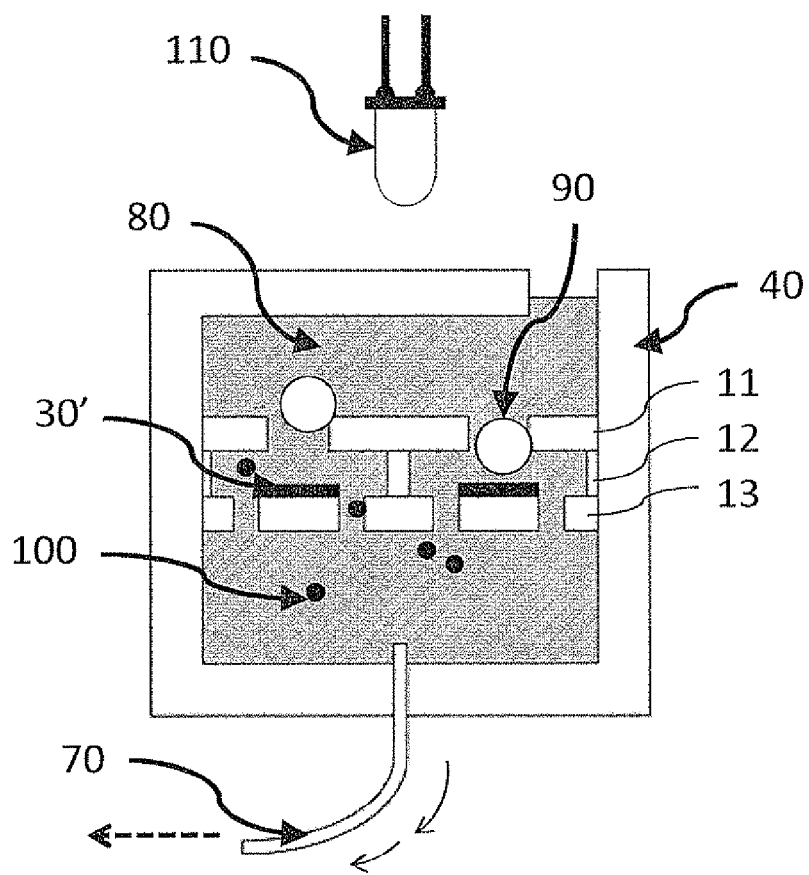
FIG. 8A is an operational view of the microparticle detecting apparatus after reaction according to the fifth embodiment of the present invention.

Then, referring to FIGS. 7A and 8A, when a sample fluid 80 (such as blood) is loaded to the first tank 41, the sample fluid 80 passes through the first mesh 111, the first separator hole 121 and the second mesh 131 in turn for separating and detecting first microparticles 90 (such as white blood cells) and second microparticles 100 (such as red blood cells). The automatic injecting/pumping device 50 is located close to the second tank 42 for providing an injecting/pumping force. And, if using the automatic injecting/pumping device 50 to pump or suck, it can accelerate the sample fluid 80 to flow from the first tank 41 into the second tanks 42.

Referring still to FIGS. 7A and 8A, when the sample fluid 80 passes through the first mesh 111, the first separator 121 and the second mesh 131 in turn, the second microparticles 100 in the sample fluid 80 fall into the second tank 42 due to pumping force during to injecting/pumping. Then, the first microparticles 90 falling into the first mesh 111 are detected and counted by the second sensor 30, wherein the light emitting unit 110 emits a light, the light is used to pass through the first mesh 111 and then be detected a value of photocurrent by the second sensor 30, so that the value of photocurrent can be further transmitted to the recording device 60 by the second sensor 30. However, when the first microparticles 90 pass through the first mesh 111 and causes the light is shaded or weakened, the second sensor 30 can detect and record a corresponding variation value of photocurrent. After, the variation value of photocurrent is transmitted to the recording device 60.

Meanwhile, it should be noted that: according to the microparticle detecting device of the present invention, the diameters of the first mesh 111 and the second mesh 131 are greater than the second microparticles 100, and the diameter of the first mesh 111 is greater than or equal to the first microparticles 90, so that the second microparticles 100 in the sample fluid 80 can pass through the microparticle detecting device and fall into the second tank 42. However, the first microparticles 90 falling into the first mesh 111 cannot pass through the second mesh 131, so that the light is shaded and a variation value of photocurrent is thus generated. Further, a photo-absorptive value of cells is exemplified, wherein the cells has one absorptive peak within a range from 200 nanometer (nm) to 350 nm of the photo-absorptive value in the wavelength field. When the cells are restricted to the first meshes 111 of the first sieve 11, of the cells shade the light emitted into the silicon (Si) photodiode sensor, so that luminous intensity of the emitting light can be identified and read by the silicon (Si) photodiode sensor for counting the cell numbers without using fluorescent detecting system. Additionally, if using different emitted lights for detecting, it only needs the cells to swallow and react with nano-materials which can absorb specific wavelengths for the purpose of detection and counting.

Figure 7B:
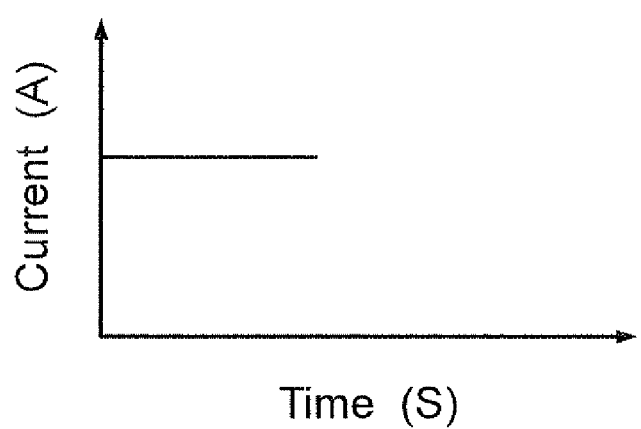
FIG. 7B is a photocurrent-time (A-S) curve diagram detected by the microparticle detecting apparatus before reaction according to the fifth embodiment of the present invention.
Figure 8B:
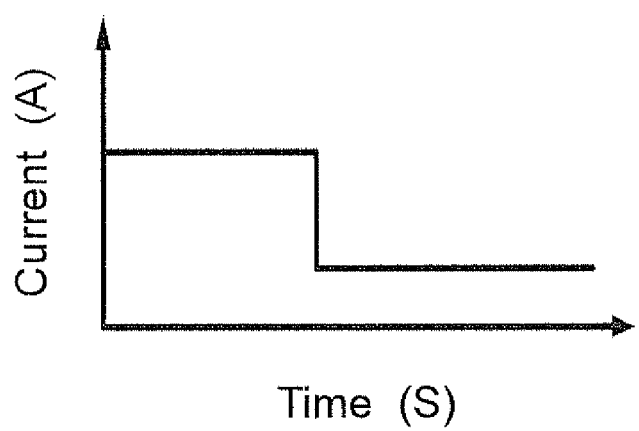
FIG. 8B is a photocurrent-time (A-S) curve diagram detected by the microparticle detecting apparatus after reaction according to the fifth embodiment of the present invention.

Moreover, referring to FIGS. 7B and 8B, in the microparticle detecting apparatus according to a fifth embodiment of the present invention, before the first microparticles 90 in the sample fluid 80 fall into the first mesh 111, the second sensor 30 detects a constant value of photocurrent (as referring to FIG. 7B) and transmits the constant value to the recording unit 60; when the sample fluid 80 is accelerated to pass the microparticle detecting apparatus by the pumping force of the automatic injecting/pumping device 50, the second microparticles 100 in the sample fluid 80 pass through the first mesh 111 and fall into the second tank 42, and thus the light is shaded in short period and only a photocurrent pulse is detected by the second sensor 30. Contrarily, the first microparticles 90 having a size equal to or greater than the diameter of the first mesh 111 fall into and locate at the first mesh 111, and thus can effectively shade the light emitted from the light emitting unit 110, so as to weaken the value of photocurrent, which is detected by the second sensor 30 detects and then transmitted to the recording device 60 for comparing with the original value of photocurrent, and then generating a variation value of photocurrent. Accordingly, it can identify if the first microparticles is detected by the microparticle detecting device. After this, the variation value of photocurrent is operated based on the concentration of the first microparticles 90 and a standard equation of photocurrent, so that a reference concentration value of the first microparticles 90 in the sample fluid 80 is obtained.

Figure 9A:
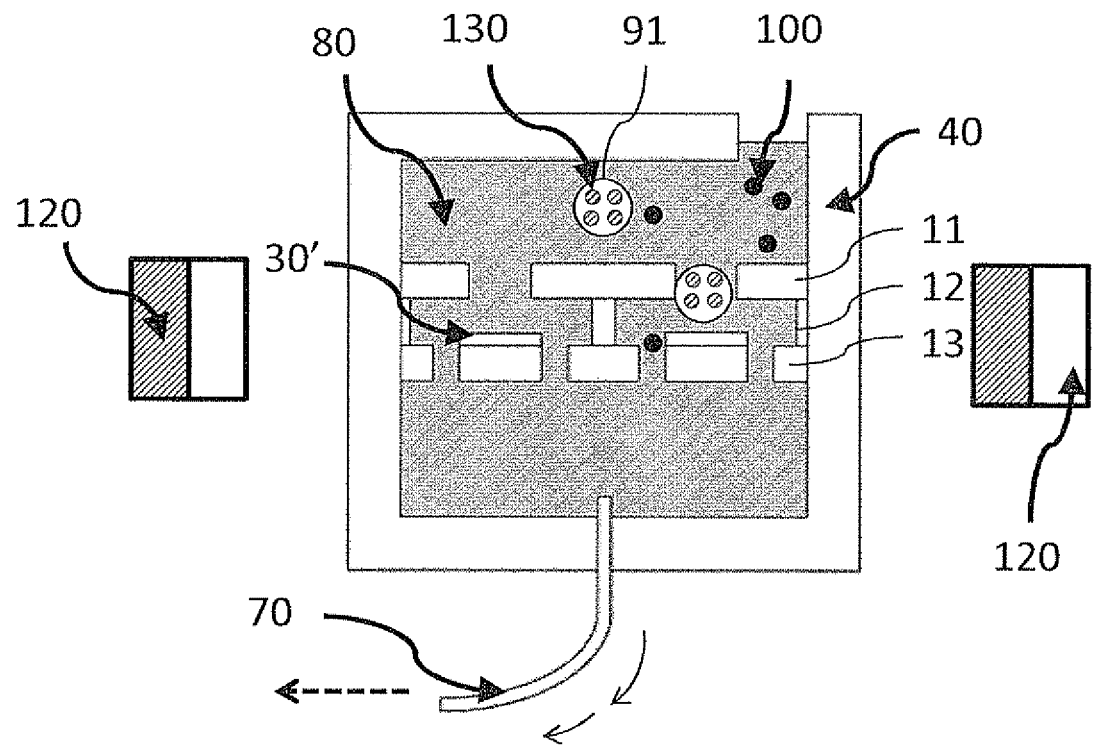
FIG. 9A is an operational view of a microparticle detecting apparatus before reaction according to a sixth embodiment of the present invention.
Figure 10A:
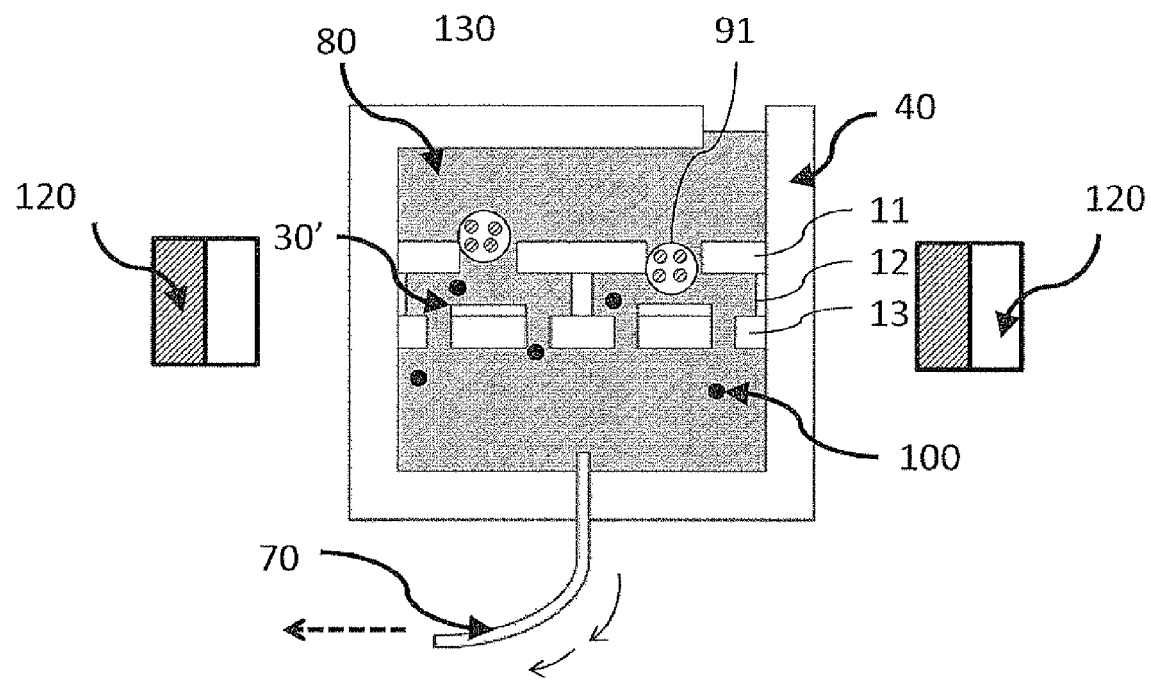
FIG. 10A is an operational view of the microparticle detecting apparatus after reaction according to the sixth embodiment of the present invention.

On the other hand, referring to FIGS. 9A and 10A, the microparticle detecting apparatus according to a sixth embodiment of the present invention is disclosed, wherein the microparticle detecting device is further cooperated with a container 40, an automatic injecting/pumping device 50 (as shown in FIG. 5), a recording device 60, two magnetic field modules 120, and a magnetic microbeads kit (not shown). The magnetic microbeads kit provides a reagent containing magnetic microbeads 130. Before detecting the microparticles in a sample fluid 80 (for example, blood), the magnetic microbeads kit must be mixed with the sample fluid 80 for a mixture reaction. And, the sample fluid 80 reacted with the magnetic microbeads is loaded into a container 40, which the microparticle detecting device is installed in. Then, the pumping function of the automatic injecting/pumping device 50 is generated to accelerate the sample fluid 80 reacted with the magnetic microbeads to pass through the first mesh 111, the first separator hole 121 and the second mesh 131 in turn. Then, the first microparticles 90 in the sample fluid 80 are labeled by the magnetic microbeads 130 and thus defined as magnetic-microbead microparticles 91.

Furthermore, in the embodiment, two magnetic field modules 120 are located at both sides of the microparticle detecting device for providing a magnetic field. The second sensor 30 is selected from a giant magnetoresistance (GMR) sensor. The second sensor 30 is used to detect a variation value of giant magnetoresistance (i.e. a variation of magnetic field) caused by the magnetic-microbead microparticles 91 passing through a space between the two magnetic field modules 120. Then, the variation value of giant magnetoresistance is transmitted to the recording device 60.

Figure 9B:
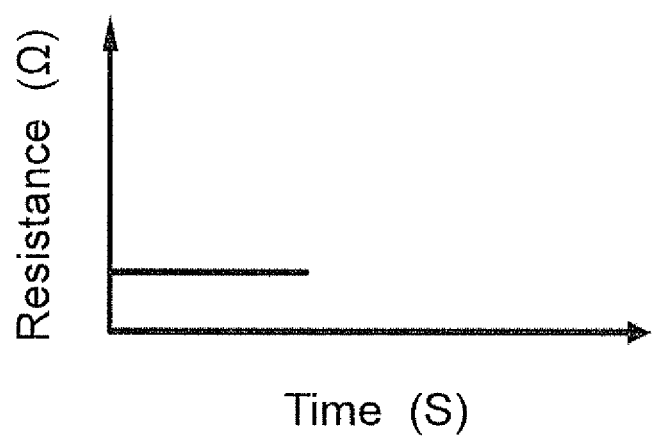
FIG. 9B is a resistances-time ($\Omega$-S) curve diagram detected by the microparticle detecting apparatus before reaction according to the sixth embodiment of the present invention.
Figure 10B:
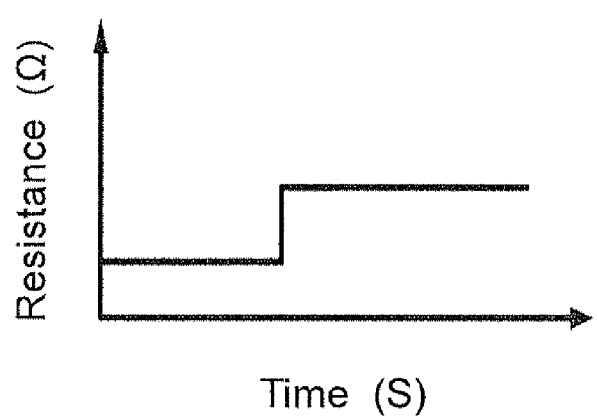
FIG. 10B is a resistances-time ($\Omega$-S) curve diagram detected by the microparticle detecting apparatus after reaction according to the sixth embodiment of the present invention.

Referring again to FIGS. 9B and 10B, after the magnetic-microbead microparticles 91 fall into and locate at the first mesh 111, the magnetic-microbead microparticles 91 absorbing the magnetic microbeads will cause the value of giant magnetoresistance ($\Omega$) detected by the second sensor 30 to change, and the variation value of giant magnetoresistance is transmitted to the recording device 60. Therefore, the numbers of the microparticles in the sample fluid 80 can be obtained. As a result, by using the giant magnetoresistance sensor to count the numbers of the cells, it is unnecessary to use fluorescent detecting system, so that the microparticle detecting device of the present invention for counting the numbers of the cells is advantageous to reduce the operation cost. Moreover, cell labeled magnetic mcirobeads can ignore drawback of fluorescents dye such photo bleaching, it means that our innovation is more robust. And, the market competitiveness of the microparticle detecting device of the present invention can be enhanced.

As described above, hemocytometer, flow cytometer, protein quantitative analysis and enzyme-linked immunosorbent assay (ELISA) of the traditional methods for counting cell numbers exist the disadvantages of personal errors, higher detection cost, complicated structure, waste of sample fluid, and so on. In contrast, the present invention is provided with the sensors 30, 20 opposite to the first or second meshes 111, 131 for detecting the microparticles in the sample fluid 80, which fall into the first mesh 11. Thus, the numbers of the target microparticles can be simultaneously detected in real-time when the target microparticles are passively separated. Therefore, the detecting processes of the sample fluid 80 can be simplified and shortened.

Furthermore, there are three methods which can be chosen to mount the sensors 20, 30 in the microparticle detecting device of the present invention provides, and the whole structure is simplifier and easier to manufacture, so that it is advantageous to expand the application field and increase the product function. Moreover, when counting the numbers of the cells by the microparticle detecting device of the present invention, the luminous intensity can be detected without adding immunofluorescent antibody for reaction. Thus, in comparison with the conventional techniques using fluorescent detecting system, the operation cost of the present invention is more economical and has higher market competitiveness.

The present invention has been described with a preferred embodiment thereof and it is understood that many changes and modifications to the described embodiment can be carried out without departing from the scope and the spirit of the invention that is intended to be limited only by the appended claims.

What is claimed is:

1. A microparticle detecting apparatus, comprising:
   at least one detection unit, each of which comprises:
   a first sieve having at least one first mesh;
   a separator stacked on one side of the first sieve and having a separator hole;
   a second sieve stacked on one side of the separator and having a plurality of second meshes, wherein the diameter of the second meshes is smaller than that of the first mesh, and the first mesh and the second meshes are misaligned with each other in a vertical direction of the first and second sieves; and
   at least one sensor aligned with the first mesh or the second meshes, and detecting microparticles falling into the first mesh or passing through the second meshes;
   wherein the at least one sensor comprises at least one second sensor, the second sensor is mounted on one side of the second sieve opposite the first mesh, and the diameter of the second sensor is greater than that of the first mesh.

2. The microparticle detecting apparatus according to claim 1, wherein materials of the first and second sieves are simultaneously selected from Si, SiC or glass.

3. The microparticle detecting apparatus according to claim 2, wherein material of the separator is selected from Si, SiC, glass, photoresist, polyimide or cyclic olefin copolymer.

4. The microparticle detecting apparatus according to claim 1, wherein the sensor comprises a plurality of first sensors, the first sensors are mounted on one side of the first sieve opposite to the second meshes, and the diameter of each of the first sensors is greater than that of each of the second meshes.

5. The microparticle detecting apparatus according to claim 1, wherein the microparticle detecting apparatus is further cooperated with a container, a recording device, an automatic injecting/pumping device and two magnetic field modules, wherein a sample fluid passes through the first meshes, the separator hole and the second meshes in turn, while the at least one sensor detects and then transmits variation values of giant magnetoresistance caused by the microparticles to the recording device for recording.

6. The microparticle detecting apparatus according to claim 5, further comprising a magnetic micro-beads kit which labels one type of the microparticles in the sample fluid to be one type of magnetic microparticles.

7. The microparticle detecting apparatus according to claim 6, wherein the sensor is selected from a giant magnetoresistance sensor, and the sensor detects and transmits the variation values of giant magnetoresistance to the recording device for recording, wherein the variation values of giant magnetoresistance are caused by the microparticles passing through a magnetic field generated from the magnetic field modules.

* * * * *